United States Patent [19]

O'Lenick

[11] Patent Number: 5,248,783
[45] Date of Patent: Sep. 28, 1993

[54] SILICONE ALKOXYLATED ESTERS CARBOXYLATE SALTS

[75] Inventor: Anthony J. O'Lenick, Lilburn, Ga.

[73] Assignee: Siltech Inc., Norcross, Ga.

[21] Appl. No.: 966,430

[22] Filed: Oct. 26, 1992

Related U.S. Application Data

[63] Continuation-in-part of Ser. No. 804,688, Dec. 11, 1991, abandoned, which is a continuation-in-part of Ser. No. 788,345, Nov. 6, 1991, abandoned.

[51] Int. Cl.$^5$ .................................................. C07F 7/10
[52] U.S. Cl. .................................... 548/110; 556/437; 554/39; 554/77
[58] Field of Search .................. 556/437; 528/26, 27, 528/28; 554/39, 77; 548/110

[56] References Cited

U.S. PATENT DOCUMENTS

| | | | |
|---|---|---|---|
| 3,922,436 | 11/1975 | Bell et al. | 556/437 X |
| 4,083,856 | 4/1978 | Mendicino | 528/27 |
| 4,352,917 | 10/1982 | Tripp | 528/26 |
| 4,584,138 | 4/1986 | Pepe et al. | 554/39 |
| 4,777,277 | 10/1988 | Colas et al. | 556/419 |
| 4,876,152 | 10/1989 | Kang | 528/26 |
| 5,087,715 | 2/1992 | Snow | 556/437 UX |
| 5,132,392 | 7/1992 | DeYoung et al. | 528/26 |
| 5,136,063 | 8/1992 | O'Lenick | 554/77 |
| 5,196,499 | 3/1993 | O'Lenick | 556/437 X |

Primary Examiner—Paul F. Shaver

[57] ABSTRACT

The invention relates to a series of novel silicone alkoxylated ester salts which contain terminal carboxyl groups which have been neutralized with various fatty amine compounds. This class of compounds provides a high dense foam and unique solubility in many organic solvents as well as very substantive salts of the carboxylic acid when neutralized with base. The compounds of the present invention are prepared by reacting a the hydroxyl group in a silicone polymer with an anhydride, followed by neutralization with an amine.

14 Claims, No Drawings

SILICONE ALKOXYLATED ESTERS CARBOXYLATE SALTS

RELATED APPLICATIONS

This application is a continuation in part of Ser. No. 07/804,688 filed Dec. 11, 1991, now abandoned, which is a continuation in part of Ser. No. 07/788,345, filed Nov. 6, 1991, now abandoned.

BACKGROUND OF THE INVENTION

1. Field of the Invention

The present invention relates to a series of novel silicone alkoxylated ester salts which have terminal carboxyl group which have been neutralized with amines. These materials provide outstanding dense foam, lubrication, and softening when applied to a variety of fiber substrates. The compounds of the present invention are prepared by reacting a hydroxyl containing silicone polymer with an anhydride and subsequently neutralizing the carboxyl group with an amine.

2. Arts and Practices

Silicone compounds have been known to be active at the surface of cellulosic and synthetic fibers as well as paper. They are good nondurable lubricants and are very stable to oxidation, however, their high cost and lack of efficiency at low concentrations as well as low durability have made their acceptance in commercial products quite low.

In addition to their high cost, silicone compounds have little or no solubility in mineral oils, fatty triglycerides and other classical fatty quaternary compounds used for softening. This has resulted in the inability to prepare stable blends for use as a textile fiber treatment.

In many applications, there is a desire for a more fatty soluble softener. The desired molecule should have the desirable softening and antistatic properties of silicone, yet have compatibility with traditional fatty materials and oils. Even though a textile softener which has both the desirable softening and antistatic properties of silicone as well as compatibility with fatty compounds has been a long felt need, it isn't until the compounds of the present invention that such a system has been attained.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is a ether linkage and a new hydroxyl group. While a definite improvement over other compounds the efficiency and durability of compounds the were not good enough to allow for cost effective incorporation of these materials in detergent formulations.

U.S. Pat. No. 4,587,320 issued to Swihart discloses that certain carboxy functional products can be prepared by equilibrating silicone glycols and a carboxy silane. The compounds of the Swihart invention because they are prepared by reacting a performed carboxy silane with a silicone glycol do not produce the desired functionality of the present invention. As will become clear from the disclosure the compounds of the present invention are carboxy functional esters of alkoxylated glycols. They are quite different in structure and in function form the Swihart compounds.

THE INVENTION

OBJECT OF THE INVENTION

It is the object of the present invention to provide novel silicone esters having a terminal carboxy group which is neutralized with an amine. These compounds are high foaming surface active agents which are also substantive to the surface of a fiber and other textile materials including cellulosic material and have increased solubility in fatty materials including mineral oil, fatty triglycerides and traditional fatty quaternary ammonium compounds. The compounds of the present invention render the lubricity, and hydrophobicity generally seen in silicone compounds, but because they are esterified with fatty groups have greater solubility in hydrocarbon oils as well as fatty materials than the traditional silicone compounds which are insoluble in those materials. The carboxy group is neutralized with amines, giving the outstanding dense foam.

It is another objective of the current invention to provide silicone ester carboxylate salts which can be used in personal care, textile, and industrial formulations to render softness and lubrication to the substrates being treated. The superior foam and solubility properties are an important benefit, since this is a major aspect of consumer perception of softness in consumer and industrial laundry applications. Application of the compounds of the invention can be from solvent, aqueous dispersion or solution, or applied neat in these processes.

SUMMARY OF THE INVENTION

The present invention relates to novel silicone alkoxylated esters which contain carboxyl groups, which are neutralized in a subsequent step with organic amines. The compounds by virtue of the salt group are high foaming surfactants. Additionally, they are soluble in fatty and hydrocarbon products, but have many of the functional softening and lubrication properties of silicone.

As will become clear from the disclosure, the compounds of the present invention while having silicone present in the molecule, have unique foaming as well as solubility properties in organic materials like triglycerides, mineral oil and the like. This property is a direct result of the structure. The pendant group needs to contain (a) a silicone atom linked covalently through carbon to (b) an alkoxylated portion linked covalently to (c) an ester function, linked covalently to (d) an R" linking group containing carbon atoms linked covalently to (E) a COOH group which is then neutralized with an organic amine. Compounds lacking these functional parts do not give the desired foaming properties.

The compounds of the present invention therefore have a pendant group which is as follows:

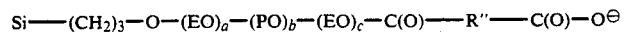

$$Si\text{---}(CH_2)_3\text{---}O\text{---}(EO)_a\text{---}(PO)_b\text{---}(EO)_c\text{---}C(O)\text{---}R''\text{---}C(O)\text{---}O^{\ominus}$$

| Silicone Group | Linkage Group | Alkoxylate Group | Ester Group | Link Group | Charged Carboxy Group |
|---|---|---|---|---|---|

The Silicone Group is soluble in silicone materials; the alkoxylate group renders water solubilty to the molecule; the ester linkage taken with the carbon linkage group make up the oil soluble group and the terminal group is the ionizable group.

These materials will allow for the solubilization of water, fatty oils and silicone oils into one phase. Standard fatty surface active agents or surfactants have only a water soluble portion and an oil soluble portion. An example is a stearyl alcohol ethoxylate.

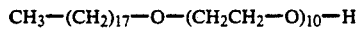

Fatty Portion | Water Soluble Portion

This type of material will allow for solubilization of fatty oils and water, but not silicones.

Silicone copolyols, on the other hand have a silicone soluble portion and a water soluble portion. These materials allow for the solubilization of silicone and water, but not in the presence of fatty oils.

Silicone Soluble Portion | Water Soluble Portion

There are many instances were there is a desire to have high dense foam and solubilize water, fatty oils and silicone into a single system. Each component is mutually insoluble in each other. Any two of the three can be solubilized by addition of a surface active agent, either conventional fatty surfactants or silicone surfactants. But conventional surfactants and silicone surfactants do not allow for the preparation of solubilized products which contain all three, only the compounds of the present invention work for all three.

The carboxy silicones of the prior art (U.S. Pat. No. 4,587,320) which lack the above mentioned groups, do not perform the solubilization properties, and do not have the same foam levels as do the compounds of the present invention perform.

The compounds of the present invention are prepared by the reaction of an anhydride with an hydroxy silicone polymer, which is the topic of the parent patent of which this is a continuation in part. Subsequently, the resulting carboxy-ester is neutralized with an organic amine, preferably a tertiary amine. Suitable amines include tri-alkyl amines, alkylamidopropylamines, imidazolines and bis 2-hydroxyethyl-alkyl amines.

Typical of the reaction of the silicone hydroxyl group with an anhydride is the following reaction;

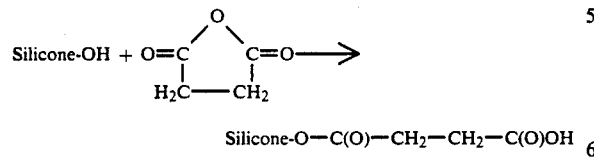

Silicone-O—C(O)—CH$_2$—CH$_2$—C(O)OH

The neutralization is then carried out either neat or in a suitable solvent like water.

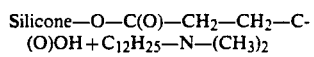

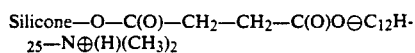

The compounds of this invention are silicone ester carboxylate salts which conform to the following structure;

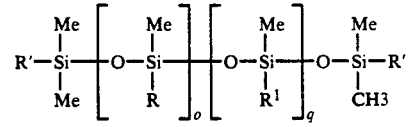

wherein;
Me is methyl;
R and R' are Methyl or
—(CH$_2$)$_3$—O—(EO)$_a$—(PO)$_b$—(EO)$_c$—C(O)—R''—C(O)O$\ominus$R$^8$;

with the proviso that both R and R' are not methyl;
R'' is selected from —CH$_2$—CH$_2$—; —CH=CH—; —CH$_2$—C(R$^7$)—H;

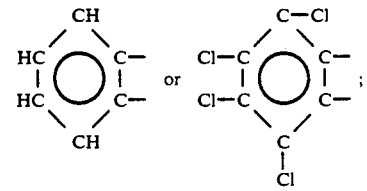

R$^7$ is alkyl having from 1 to 20 carbon atoms;
R$^1$ is selected from lower alkyl CH$_3$(CH$_2$)$_n$— or phenyl;
n is an integer from 0 to 8;
a, b and c are integers independently ranging from 0 to 20;
EO is an ethylene oxide residue —(CH$_2$CH$_2$—O)—;
PO is a propylene oxide residue —(CH$_2$CH(CH$_3$)—O)—;
o is an integer ranging from 1 to 100;
q is an integer ranging from 0 to 500;
R$^8$ is selected from

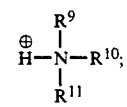

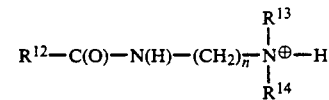

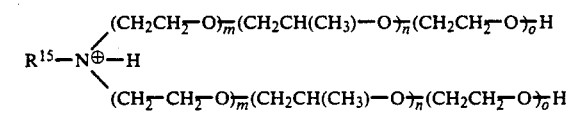

or

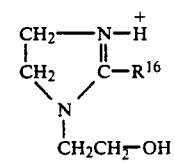

R$^9$ is alkyl having from 1 to 20 carbon atoms;
R$^{10}$ is alkyl having from 1 to 20 carbon atoms;
R$^{11}$ is alkyl having from 1 to 20 carbon atoms;

$R^{12}$ is alkyl having from 1 to 20 carbon atoms;
$R^{13}$ and $R^{14}$ are independently selected from lower alkyl having from one to three carbon atoms;
$R^{15}$ is alkyl having from 6 to 20 carbon atoms;
$R^{16}$ is alkyl having from 6 to 20 carbon atoms;
m, n, and o are independently integers each ranging from 0 to 20.

PREFERRED EMBODIMENTS

In a preferred embodiment, a+b+c is greater than zero. This proviso requires that the silicone be alkoxylated and results in improved foam and solubilization properties for the silicone in oils.

In another preferred embodiment, the R" is —CH$_2$—CH$_2$—.

In still another embodiment R" is —CH=CH—.

In another preferred embodiment R" is —CH$_2$—C($R^7$)—H.

In still another preferred embodiment R" is

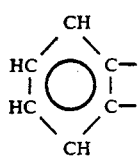

In still another preferred embodiment R" is

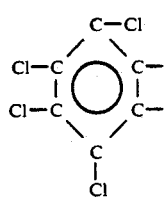

In still another preferred embodiment $R^7$ is alkyl having from 6 to 20 carbon atoms.

In a more preferred embodiment $R^7$ is alkyl having from 12 to 20 carbon atoms.

In a preferred embodiment $R^8$ is

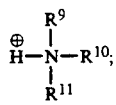

$R^9$ is alkyl having from 1 to 20 carbon atoms;
$R^{10}$ is alkyl having from 1 to 20 carbon atoms;
$R^{11}$ is alkyl having from 1 to 20 carbon atoms.

In a preferred embodiment $R^8$ is

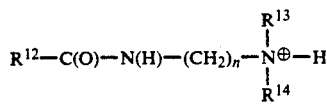

$R^{12}$ is alkyl having from 1 to 20 carbon atoms;
$R^{13}$ and $R^{14}$ are independently selected from lower alkyl having from one to three carbon atoms.

In a preferred embodiment $R^8$ is

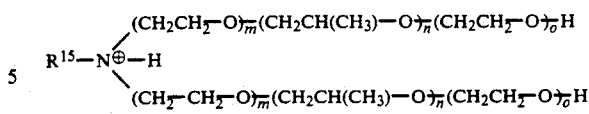

$R^{15}$ is alkyl having from 6 to 20 carbon atoms;
m, n, and o are independently integers each ranging from 0 to 20.

In a preferred embodiment $R^8$ is

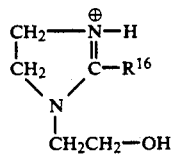

$R^{16}$ is alkyl having from 6 to 20 carbon atoms.

EXAMPLES

The compounds of the present invention are prepared by the reaction of a hydroxy silicone compound and an anhydride. Examples of suitable reactants are as follows;

REACTANTS

Anhydrides

The various anhydrides listed are all items of commerce and are prepared by methods known to those skilled in the art.

Reactant Example I

Succinic Anhydride

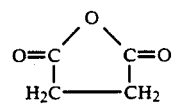

Reactant Example II

Alkyl Succinic Anhydride

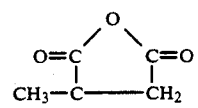

Reactant Example III

Alkyl Succinic Anhydride

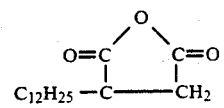

Reactant Example IV

Alkyl Succinic Anhydride

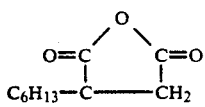

Reactant Example V

Alkyl Succinic Anhydride

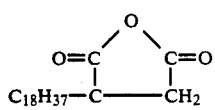

Reactant Example VI

Alkyl Succinic Anhydride

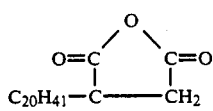

Reactant Example VII

Maleic Anhydride

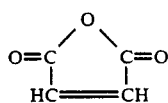

Reactant Example VIII

Phthalic Anhydride

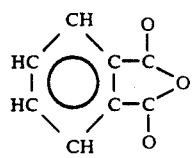

Reactant Example IX

Tetrachlorophthalic anhydride

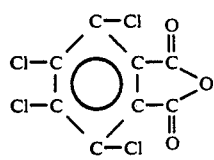

Hydroxy Silicone Compounds

Many manufacturers offer a series of hydroxy silicone compounds suitable for use as raw materials in the preparation of the esters of the present invention. These materials are marketed under the many trade names. Siltech Inc. of Norcross, Ga., Union Carbide of Danbury, Conn. and Dow Corning of Midland, Mich., offer these compounds commercially.

The preferred method of placing this type of reactive hydroxyl group into the silicone polymer is by the reaction of silanic hydrogen containing polymer with allyl alcohol alkoxylates. This technology is well known to those skilled in the art and are described in U.S. Pat. No. 4,083,856. These hydroxyl functional silicone compounds are subsequently reacted with anhydrides, to make the compounds of the present invention.

Additionally, hydroxy silicone compounds are available from Siltech Inc. Norcross, Ga. These compounds conform to the following generic structure;

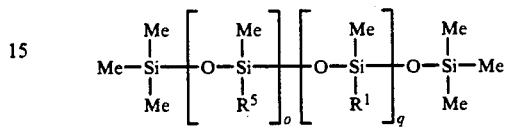

wherein
Me is methyl;
$R^5$ is $-(CH_2)_3-O-(EO)_a-(PO)_b-(EO)_c-H$
$R^1$ is selected from lower alkyl $CH_3(CH_2)_n-$ or phenyl;
n is an integer from 0 to 8;
a, b and c are integers independently ranging from 0 to 20;
EO is an ethylene oxide residue $-(CH_2CH_2-O)-$;
PO is a propylene oxide residue $-(CH_2CH(CH_3)-O)-$;
o is an integer ranging from 1 to 100;
q is an integer ranging from 0 to 500.

| Example | Name | a | b | c | o | q |
|---|---|---|---|---|---|---|
| 1 | Siltech H 1000 | 3 | 0 | 0 | 2 | 54 |
| 2 | Siltech H 1100 | 10 | 5 | 10 | 10 | 100 |
| 3 | Siltech H 1200 | 20 | 20 | 20 | 2 | 56 |
| 4 | Siltech H 1300 | 10 | 10 | 10 | 6 | 26 |
| 5 | Siltech H 1400 | 0 | 10 | 0 | 4 | 200 |
| 6 | Siltech H 1500 | 5 | 5 | 5 | 2 | 50 |
| 7 | Siltech H 1600 | 0 | 6 | 0 | 10 | 25 |
| 8 | Siltech H 1700 | 0 | 0 | 0 | 5 | 10 |

Terminal Substituted Dimethicone Copolyol Compounds

Terminal substituted dimethicone copolyol compounds are well known and are marketed in the trade under many names.

The preferred method of placing this type of reactive hydroxyl group into the silicone polymer is by the reaction of terminal silanic hydrogen containing polymer with allyl alcohol alkoxylates. This technology is well known to those skilled in the art and are described in U.S. Pat. No. 4,083,856.

These materials are available from Siltech Inc. Norcross, Ga. and are marketed under the Siltech T series trade name.

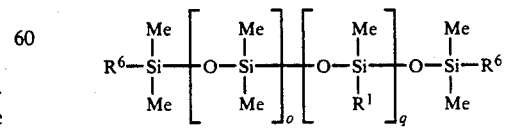

wherein;
Me is methyl;
$R^6$ is $-(CH_2)_3-O-(EO)_a-(PO)_b-(EO)_c-H$
$R^1$ is selected from lower alkyl $CH_3(CH_2)_n-$ or phenyl;

n is an integer from 0 to 8;
a, b and c are integers independently ranging from 0 to 20;
EO is an ethylene oxide residue —$(CH_2CH_2-O)$—;
PO is a propylene oxide residue —$(CH_2CH(CH_3)-O)$—;
o is an integer ranging from 1 to 100;
q is an integer ranging from 0 to 500.

| Example | Name | a | b | c | Equivalent Molecular Weight |
|---|---|---|---|---|---|
| 9 | Siltech T 701 | 0 | 0 | 0 | 1,000 |
| 10 | Siltech T 706 | 5 | 1 | 0 | 6,000 |
| 11 | Siltech T 710 | 2 | 1 | 1 | 10,000 |
| 12 | Siltech T 750 | 10 | 5 | 10 | 50,000 |
| 13 | Siltech T 790 | 20 | 20 | 20 | 86,000 |

General Reaction Conditions;

The reaction can be run with either a stiochiometric amount of the anhydride, or an excess of silicone polymer.

Into a suitable round bottom, three neck flask equipped with a thermometer and a nitrogen sparge is added the specified number of grams of the specified silicone compound and the specified number of grams of the specified anhydride. The reaction mass is blanketed with nitrogen, and heated to 80 and 110 C. under the inert nitrogen blanket. Within four to five hours the theoretical acid value is obtained. The product is a clear liquid and is used without additional purification.

EXAMPLE 14

Into a suitable round bottom, three neck flask equipped with a thermometer and a nitrogen sparge is added number 100.0 grams of silicone example 1 and the 1,000.0 grams of succinic anhydride. The reaction mass is then blanketed with nitrogen and heated to 80 and 110 C. This temperature is maintained for four to five hours. The theoretical acid value is obtained. The product is a clear liquid and is used without additional purification.

EXAMPLES 15-32

Example 14 is repeated only this time substituting the specified number of grams of the anhydride specified and the specified type and number of grams of silicone compound as shown below;

| Example | Anhydride Reactant Example | Grams | Silicone Compound Example | Grams |
|---|---|---|---|---|
| 15 | I | 100.0 | 1 | 2,329.0 |
| 16 | II | 115.0 | 2 | 2,032.0 |
| 17 | III | 269.0 | 3 | 5,129.0 |
| 18 | IV | 185.0 | 4 | 347.6 |
| 19 | V | 316.0 | 5 | 4,407.0 |
| 20 | VI | 340.0 | 6 | 2,743.0 |
| 21 | VII | 98.0 | 7 | 3,550.8 |
| 22 | VIII | 148.0 | 8 | 1,512.4 |
| 23 | IX | 288.0 | 9 | 1,000.0 |
| 24 | I | 100.0 | 10 | 6,000.0 |
| 25 | II | 115.0 | 11 | 10,000.0 |
| 26 | III | 269.0 | 12 | 50,000.0 |
| 27 | IV | 185.0 | 13 | 86,000.0 |
| 28 | V | 316.0 | 1 | 2,329.0 |
| 29 | VI | 340.0 | 2 | 2,032.0 |
| 30 | VII | 98.0 | 3 | 5,129.0 |
| 31 | VIII | 148.0 | 4 | 347.6 |
| 32 | IX | 288.0 | 5 | 4,407.0 |

NEUTRALIZATION REACTION

The specified amount of the specified carboxy-silicone compounds prepared according to examples 1-32 are neutralized with the specified amount of the specified amine. Typically, the neutralization is carried out in water or other protic solvent. Typical concentrations of the product range from 20-80% with 35-50 being preferred.

Raw Material Amines
Class 1 Alkyl Tertiary amines

$R^9$ is alkyl having from 1 to 20 carbon atoms;
$R^{10}$ is alkyl having from 1 to 20 carbon atoms;
$R^{11}$ is alkyl having from 1 to 20 carbon atoms;

| Raw Material Example | $R^9$ | $R^{10}$ | $R^{11}$ | Molecular Weight |
|---|---|---|---|---|
| A | Me | $C_{12}H_{25}$ | Me | 213.0 |
| B | $C_2H_5$ | $C_6H_{13}$ | $C_2H_5$ | 143.0 |
| C | Me | $C_8H_{17}$ | Me | 143.0 |
| D | Me | $C_{10}H_{21}$ | Me | 171.0 |
| E | Me | $C_{18}H_{37}$ | Me | 283.0 |
| F | Me | $C_{20}H_{41}$ | Me | 311.0 |
| G | $C_6H_{13}$ | $C_6H_{13}$ | Me | 185.0 |
| H | Me | $C_{10}H_{21}$ | $C_{10}H_{21}$ | 297.0 |

Class 2 Alkyl amido Amines

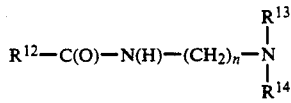

$R^{12}$ is alkyl having from 1 to 20 carbon atoms;
$R^{13}$ and $R^{14}$ are independently selected from lower alkyl having from one to three carbon atoms.

| Raw Material Example | $R^{12}$ | $R^{13}$ | $R^{14}$ | Molecular Weight |
|---|---|---|---|---|
| I | $C_7H_{15}$ | Me | Me | 129.0 |
| J | $C_{11}H_{23}$ | Me | Me | 185.0 |
| K | $C_{13}H_{27}$ | Me | Me | 213.0 |
| L | $C_{17}H_{35}$ | Me | Me | 269.0 |
| M | $C_{19}H_{39}$ | $C_2H_5$ | $C_2H_5$ | 325.0 |
| N | $C_6H_{13}$ | $C_2H_5$ | $C_2H_5$ | 143.0 |
| O | $C_{20}H_{41}$ | $C_2H_5$ | $C_2H_5$ | 319.0 |
| P | $C_{11}H_{23}$ | $C_2H_5$ | $C_2H_5$ | 213.0 |

Class 3 Alkyl (N) bis hydroxy amines

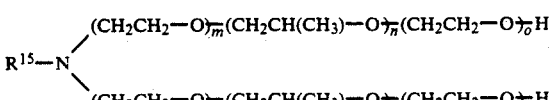

$R^{15}$ is alkyl having from 6 to 20 carbon atoms;
m, n, and o are independently integers each ranging from 0 to 20.

| Raw Material Example | $R^{15}$ | m | n | o | Molecular Weight |
|---|---|---|---|---|---|
| Q | $C_6H_{13}$ | 20 | 20 | 20 | 3,039.0 |
| R | $C_{10}H_{21}$ | 0 | 0 | 0 | 155.0 |
| S | $C_{12}H_{25}$ | 5 | 1 | 5 | 682.0 |
| T | $C_{18}H_{37}$ | 0 | 10 | 0 | 857.0 |
| U | $C_{20}H_{41}$ | 5 | 1 | 10 | 994.0 |

Class 4 Imidazoline Amines

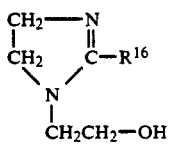

$R^{16}$ is alkyl having from 6 to 20 carbon atoms.

| Raw Material Example | $R^{16}$ | Molecular Weight |
|---|---|---|
| V | $C_7H_{15}$ | 186.0 |
| W | $C_{11}H_{23}$ | 242.0 |
| X | $C_{17}H_{35}$ | 326.0 |
| Y | $C_{19}H_{40}$ | 355.0 |
| Z | $C_6H_{13}$ | 172.0 |

NEUTRALIZATION

EXAMPLE 33

For purposes of example, the products presented will be in water at 50% solids. That is water in a concentration equal to the weight of each reactant is first added to a suitable mixing vessel. To the water is added the above amount of the above identified product example 14. Subsequently, 106.5 grams of amine reactant "A" is added under good agitation.

EXAMPLES 34-84

Example 33 is repeated, only this time the specifies amount of the specified carboxy intermediate is substituted for Example 14 and the specified amount and type of amine is substituted with the specified type and amount of amine. As before, the amount of added water equals the sum of both added components. This results in a concentration of 50% for the final product which is used without purification.

| Example Number | Carboxy Intermediate Example | Amine Example | Reactant Grams |
|---|---|---|---|
| 34 | 15 | B | 71.5 |
| 35 | 16 | C | 71.5 |
| 36 | 17 | D | 85.5 |
| 37 | 18 | E | 141.5 |
| 38 | 19 | F | 155.5 |
| 39 | 20 | G | 92.5 |
| 40 | 21 | H | 148.5 |
| 41 | 22 | I | 64.5 |
| 42 | 23 | J | 92.5 |
| 43 | 24 | K | 106.5 |
| 44 | 25 | L | 134.5 |
| 45 | 26 | M | 229.8 |
| 46 | 27 | N | 71.5 |
| 47 | 28 | O | 319.0 |
| 48 | 29 | P | 213.0 |
| 49 | 30 | Q | 3,039.0 |
| 50 | 31 | R | 155.0 |
| 51 | 32 | S | 682.0 |
| 52 | 14 | T | 857.0 |
| 53 | 15 | U | 994.0 |
| 54 | 16 | V | 186.0 |
| 55 | 17 | W | 242.0 |
| 56 | 18 | X | 326.0 |
| 57 | 19 | Y | 355.0 |
| 58 | 20 | Z | 172.0 |
| 59 | 21 | A | 213.0 |
| 60 | 22 | B | 143.0 |
| 61 | 23 | C | 143.0 |
| 62 | 24 | D | 171.0 |
| 63 | 25 | E | 283.0 |
| 64 | 26 | F | 311.0 |
| 65 | 27 | G | 185.0 |
| 66 | 28 | H | 297.0 |
| 67 | 29 | I | 129.0 |
| 68 | 30 | J | 185.0 |
| 69 | 31 | K | 213.0 |
| 70 | 32 | L | 269.0 |
| 71 | 33 | M | 325.0 |
| 72 | 34 | N | 143.0 |
| 73 | 35 | O | 159.5 |
| 74 | 36 | P | 106.5 |
| 75 | 37 | Q | 1,519.5 |
| 76 | 38 | R | 77.5 |
| 77 | 39 | S | 341.0 |
| 78 | 40 | T | 428.5 |
| 79 | 41 | U | 497.0 |
| 80 | 42 | V | 93.0 |
| 81 | 15 | W | 121.0 |
| 82 | 16 | X | 163.0 |
| 83 | 17 | Y | 177.5 |
| 84 | 18 | Z | 86.0 |

APPLICATIONS EXAMPLES

The compounds of the present invention produce a copious thick foam when diluted to 1% active in cylinder shake foam tests. The compounds have been found to increase and stabilize the foam when the compounds are added at 5% concentration to sodium lauryl sulfate.

The compounds of the present invention are very mild to the skin, eyes and mucous membrane when applied at 10% active. Surprisingly, the compounds of the present invention also mitigate irritation of alkyl sulfates when added to these irritating products.

The compounds of the present invention are not toxic when tested in LD 50 tests.

All of these attributes make the compounds of the present invention candidates for use in personal care compositions.

What is claimed;

1. A silicone compound which conforms to the following structure;

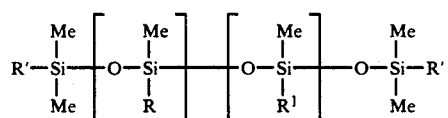

wherein;
Me is methyl;
R and R' are methyl or

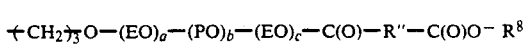

with the proviso that both R and R' are not methyl;

R″ is selected from —CH$_2$—CH$_2$—; —CH=CH—; —CH$_2$—C(R$^7$)—H;

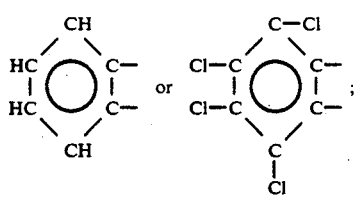

R$^7$ is alkyl having from 1 to 20 carbon atoms;
R$^1$ is selected from lower alkyl CH$_3$(CH$_2$)$_n$— or phenyl;
n is an integer from 0 to 8;
a, b and c are integers independently ranging from 0 to 20;
EO is an ethylene oxide residue —(CH$_2$CH$_2$—O)—;
PO is a propylene oxide residue —(CH$_2$CH(CH$_3$)—O)—;
o is an integer ranging from 1 to 100;
q is an integer ranging from 0 to 500;
R$^8$ is selected from

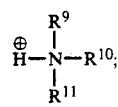

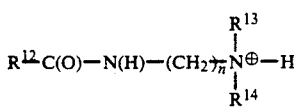

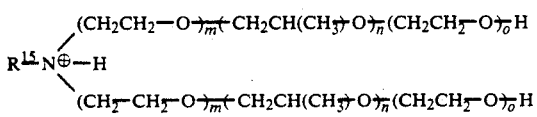

or

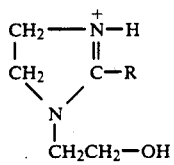

R$^9$ is alkyl having from 1 to 20 carbon atoms;
R$^{10}$ is alkyl having from 1 to 20 carbon atoms;
R$^{11}$ is alkyl having from 1 to 20 carbon atoms;
R$^{12}$ is alkyl having from 1 to 20 carbon atoms;
R$^{13}$ and R$^{14}$ are independently selected from lower alkyl having from one to three carbon atoms;
R$^{15}$ is alkyl having from 6 to 20 carbon atoms;
R$^{16}$ is alkyl having from 6 to 20 carbon atoms;
m, n, and o are independently integers each ranging from 0 to 20.

2. A compound of claim 1 wherein R$^8$ is;

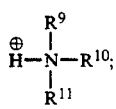

R$^9$ is alkyl having from 1 to 20 carbon atoms;

R$^{10}$ is alkyl having from 1 to 20 carbon atoms;
R$^{11}$ is alkyl having from 1 to 20 carbon atoms.

3. A compound of claim 1 wherein R$^8$ is;

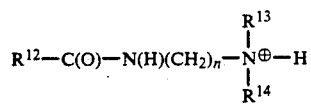

R$^{12}$ is alkyl having from 1 to 20 carbon atoms;
R$^{13}$ and R$^{14}$ are independently selected from lower alkyl having from one to three carbon atoms.

4. A compound of claim 1 wherein R$^8$ is;

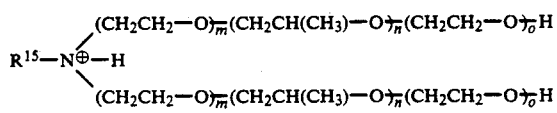

R$^{15}$ is alkyl having from 6 to 20 carbon atoms;
m, n, and o are independently integers each ranging from 0 to 20.

5. A compound of claim 1 wherein R$^8$ is;

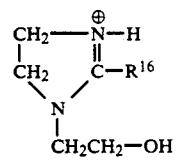

R$^{16}$ is alkyl having from 6 to 20 carbon atoms.

6. A compound of claim 1 wherein R″ is —CH$_2$—CH$_2$—.

7. A compound of claim 1 wherein R″ is —CH=CH—.

8. A compound of claim 1 wherein R″ is —CH$_2$—C(R$^7$)—H.

9. A compound of claim 1 wherein R″ is

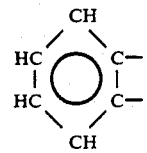

10. A compound of claim 1 wherein R″ is

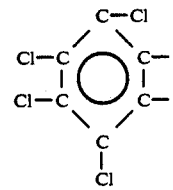

11. A compound of claim 1 wherein x, y and z are each zero.

12. A compound of claim 2 wherein x, y and z are each zero.

13. A compound of claim 3 wherein x, y and z are each zero.

14. A compound of claim 4 wherein x, y and z are each zero.

* * * * *